(12) United States Patent
Uchi et al.

(10) Patent No.: US 8,496,826 B2
(45) Date of Patent: Jul. 30, 2013

(54) BODY FLUID TREATING DEVICE OF HOLLOW FIBER MEMBRANE TYPE

(75) Inventors: Yukihiko Uchi, Shizuoka (JP); Makoto Fukuda, Oita (JP); Satoshi Uezumi, Oita (JP); Hidetoshi Hidaka, Oita (JP); Takayasu Fujimura, Shizuoka (JP)

(73) Assignee: Asahi Kasei Medical Co., Ltd., Tokyo (JP)

(*) Notice: Subject to any disclaimer, the term of this patent is extended or adjusted under 35 U.S.C. 154(b) by 533 days.

(21) Appl. No.: 10/553,950

(22) PCT Filed: Apr. 23, 2004

(86) PCT No.: PCT/JP2004/005870
§ 371 (c)(1),
(2), (4) Date: May 19, 2006

(87) PCT Pub. No.: WO2004/094047
PCT Pub. Date: Nov. 4, 2004

(65) Prior Publication Data
US 2007/0007193 A1   Jan. 11, 2007

(30) Foreign Application Priority Data

Apr. 23, 2003 (JP) ................................. 2003-118950
Apr. 23, 2003 (JP) ................................. 2003-118951

(51) Int. Cl.
*B01D 63/02* (2006.01)
*B01D 61/24* (2006.01)

(52) U.S. Cl.
USPC .............. 210/321.89; 210/321.8; 210/321.87; 210/321.88; 210/645; 210/646

(58) Field of Classification Search
USPC .............. 210/321.79–321.81, 321.87–321.89
See application file for complete search history.

(56) References Cited

U.S. PATENT DOCUMENTS 4,201,673 A * 5/1980 Kanno et al. ............. 210/321.81
4,620,965 A   11/1986 Fukusawa et al.
(Continued)

FOREIGN PATENT DOCUMENTS

EP   0306613    3/1989
JP   44-5526    3/1969
(Continued)

OTHER PUBLICATIONS

An English language abstract of patent family member Japanese Laid-open Patent Publication No. HEI 4-227030.

(Continued)

*Primary Examiner* — Katherine Zalasky
(74) *Attorney, Agent, or Firm* — Greenblum & Bernstein P.L.C.

(57) ABSTRACT

A hollow fiber membrane type fluid treatment device having at least a body portion of tubular housing containing a hollow fiber membrane bundle. In the hollow fiber membrane type fluid treatment device, an inner surface of a body portion of the tubular housing at a side of a treatment liquid inlet has a body straight portion and an end tapered portion which increases in diameter toward an end face of the housing body portion, the hollow fiber membrane is arranged so that a distance between the hollow fiber membranes is gradually increased toward the end face on the treatment liquid inlet side along a taper of a tapered portion of the inner surface of the housing body portion, and a liquid to be treated flows within the hollow fiber membranes and a treatment liquid flows outside of the hollow fiber membranes.

5 Claims, 4 Drawing Sheets

U.S. PATENT DOCUMENTS

| | | |
|---|---|---|
| RE33,932 E | 5/1992 | Fukasawa et al. |
| 2003/0028073 A1 | 2/2003 | Mochizuki et al. |

FOREIGN PATENT DOCUMENTS

| | | |
|---|---|---|
| JP | 53-31828 | 3/1978 |
| JP | 3151168 | 4/1978 |
| JP | 57-194007 | 11/1982 |
| JP | 59-4403 | 1/1984 |
| JP | 59-18084 | 4/1984 |
| JP | 63-56044 | 4/1988 |
| JP | 8-173527 | 7/1996 |
| JP | 8173527 | 7/1996 |
| JP | 8-246283 | 9/1996 |
| JP | 2000-42100 | 2/2000 |
| JP | 3080430 | 6/2000 |
| JP | 2000-350781 | 12/2000 |
| JP | 2003-102833 | 4/2003 |
| JP | 2003-111836 | 4/2003 |
| WO | 01/60477 | 8/2001 |

OTHER PUBLICATIONS

An English language abstract of patent family member Japanese Laid-open Patent Publication No. SHO 53-35683.
English language Abstract of JP 57-194007.
English language Abstract of JP 8-246283.
English language Abstract of JP 8173527.
English language Abstract of JP 10-305218.
English language Abstract of JP 59-4403.
English language Abstract of JP 2000-42100.
English language Abstract of JP 2000-350781.
English language Abstract of JP 2003-102833.
English language Abstract of JP 2003-111836.

* cited by examiner

BODY FLUID TREATING DEVICE OF HOLLOW FIBER MEMBRANE TYPE

TECHNICAL FIELD

The present invention relates to a novel hollow fiber membrane type fluid treatment device containing a hollow fiber membrane bundle. More particularly, the present invention relates to a hollow fiber membrane type fluid treatment device suitably used in the medical field or the like as a fluid treatment device exhibiting excellent purification performance of body fluid.

BACKGROUND ART

As a hollow fiber membrane type fluid treatment device including a tubular housing containing a hollow fiber membrane bundle, a hemodialyzer, hemofilter, hemodiafilter, and plasma separator used for hemodialysis, hemofiltration, and the like have been known. For example, a hemodialyzer removes wastes or toxic substances accumulated in blood based on the principle of diffusion, filtration, or the like. The hemodialyzer was put into practical use as a drum-type hemodialyzer in the middle of the twentieth century, and has been effectively still utilized for treatment of a patient suffering from partial or complete kidney failure. In general, wastes or toxic substances are removed mainly through a membrane. As the material for the membrane, regenerated cellulose and synthetic polymers such as polyacrylonitrile, polysulfone, and polyethylene have been known. As the shape of the membrane, a flat membrane and a hollow fiber membrane can be given. In recent years, a hollow fiber membrane which allows an increase in the contact area with blood and exhibits high purification performance has been widely used.

When manufacturing a hemodialyzer by using a hollow fiber membrane, several hundred to several tens of thousand hollow fiber membranes are bundled and placed in a plastic tubular housing. The housing is then filled with a potting material such as a polyurethane resin to fix the hollow fiber membranes to the housing. The resulting semifabricated product is provided with a blood introducing part (header cap) and sterilized to obtain a hemodialyzer. When treating blood by using a hemodialyzer utilizing a hollow fiber membrane, blood is caused to flow inside the hollow fiber membrane, and a dialysate containing an inorganic electrolyte or the like is caused to flow outside the hollow fiber membrane to remove wastes or toxic substances in the blood into the dialysate by utilizing the diffusion or filtration principle.

Substance removal performance is used as an index which indicates the removal performance of wastes or toxic substances in the blood of the hemodialyzer. The main factor which determines the substance removal performance is the performance, that is, the mass transfer coefficient, of the hollow fiber membrane which directly comes into contact with the blood or dialysate. Therefore, the material for the hollow fiber membrane, the size and distribution of the pores which allow a substance to pass therethrough, the thickness of the membrane which determines the permeation resistance, and the like have been studied and put in practical use.

In order to allow the hollow fiber membrane to exhibit the maximum substance removal performance, it has been mainly studied from two viewpoints of an improvement of the hollow fiber membrane bundle and an improvement of the structure and shape of the housing. For example, as for the former the optimization of the fiber density, which indicates the ratio of the cross-sectional area of the hollow fiber membrane bundle to the cross-sectional area of the tubular housing, and as for the latter the relationship between the length and the inner diameter of the housing have been studied and put in practical use. However, a conventional hemodialyzer exhibits insufficient substance removal performance, since the dialysate does not uniformly flow between the hollow fiber membranes.

In order to improve the substance removal performance and reduce the variation in the removal performance by causing the dialysate to uniformly flow through the hollow fiber membrane bundle, Japanese Patent No. 3080430, Japanese Examined Patent Publication (Kokoku) No. 59-18084, and Japanese Patent Application Laid-open No. 8-246283 disclose a technology of placing a spacer filament between the hollow fiber membranes. Furthermore, Japanese Patent Application Laid-open No. 57-194007 and WO 01/60477 disclose a technology of forming the hollow fiber membrane into a small wave shape called a crimp. These technologies aim at obtaining a uniform flow of the dialysate by creating a certain space between the hollow fiber membranes and preventing an uneven flow of the dialysate. However, in the case of forming the hollow fiber membrane bundle provided with a spacer filament, a complicated technology is required to insert the spacer filament between the hollow fiber membranes or knit the hollow fiber membrane with the spacer filament. In the case of forming the crimped hollow fiber membrane, the hollow fiber membrane breaks at the waved section or is plugged up, whereby productivity is decreased.

As to the structure and shape of the housing, Japanese Patent Application Laid-open No. 8-173527 discloses a housing shape which prevents the dialysate from remaining in the housing for a long time to obtain a uniform flow in consequence. In this technology, an inclined transition portion is provided between the end portion and the center portion of the housing, and the inclination angle continuously changes in the circumferential direction. However, since the dialysate does not uniformly flow into between the hollow fiber membranes in the vicinity of the dialysate inlet even when using this method, sufficient substance removal performance cannot be obtained. Moreover, since the space in the vicinity of the dialysate inlet of the housing is remarkably nonuniform structure, there is also a problem that a desired effect cannot be obtained when the flow rate of the dialysate is changed.

As described above, the conventional approach concerning the hollow fiber membrane and the housing shape in order to improve the substance removal performance of the hemodialyzer by making the dialysate flow uniform involves problems respectively, and the effect is not necessarily satisfactory.

In the hollow fiber membrane type fluid treatment device, if the hollow fiber membrane breaks, the treatment target liquid comes into contact with the treatment liquid, whereby a desired separation cannot be achieved. In the case where the treatment target liquid is blood, the blood flows outside the body. Therefore, the hollow fiber membrane must not be broken from the viewpoint of safety.

Various technical means have been proposed to prevent breakage of the hollow fiber membrane, particularly in the vicinity of the end portion of the hollow fiber membrane. An improvement of the hollow fiber membrane (bundle) and an improvement of the structure and shape of the housing have been mainly studied in the same manner as in the case of improving the substance removal performance.

As to a hollow fiber membrane, for example, Japanese Patent No. 3151168 and Japanese Patent Application Laid-open No. 59-4403 disclose a technology of reducing stress concentration by partially reinforcing the hollow fiber membrane. Specifically, in order to prevent occurrence of leakage by reducing both impacts due to a water stream or dropping in the hollow fiber membrane module, a resin coating layer is provided over the circumference of the hollow fiber bundle from the inner side of the resin layer on both ends of the hollow fiber membrane bundle to a position corresponding to the treatment liquid inlet and the treatment liquid outlet. However, since a very long coating layer is necessary for ensuring sufficient leakage resistance performance, the membrane area effective for substance exchange may be reduced, and the flow of the treatment liquid which flows outside the hollow fiber membrane may be affected by the provided coating layer. As a result, the removal performance of the hollow fiber membrane module may be decreased.

As to the hollow fiber membrane bundle, Japanese Patent No. 3151168 discloses a method for preventing occurrence of leakage due to breakage of the hollow fiber membrane bundle as a conventional technology by increasing the fiber density of the hollow fiber membrane bundle (i.e. the ratio of the sum of the cross-sectional areas of the hollow fiber membranes to the cross-sectional area of the tubular housing) at positions corresponding to the treatment liquid inlet and the treatment liquid outlet in the tubular housing and reducing vibration of the hollow fiber membranes due to the flow of the treatment liquid. However, as described above Japanese Patent, since it becomes very difficult to place the hollow fiber membrane bundle in the tubular housing if the fiber density is increased excessively, breakage of the hollow fiber membrane may occur when placing the hollow fiber membrane bundle in the tubular housing. Therefore, in the hollow fiber membrane module disclosed in Japanese Patent Application Laid-open No. 59-4403, the fiber density is disclosed to set in a range as low as 34 to 41%. However, since the dialysate tends to bring a short-path if the fiber density is low, this method is not necessarily preferable from the viewpoint of the substance removal performance.

A number of studies have been made about a baffle plate that is provided for preventing a water stream from directly coming into contact with the hollow fiber membrane located at the treatment liquid inlet or outlet. For example, Japanese Patent Application Laid-open No. 2000-42100 aims at preventing occurrence of breakage by increasing the space between the baffle plate and the side surface of the hollow fiber membrane bundle in the vicinity of a tongue-shaped baffle plate disposed corresponding to the treatment liquid inlet or outlet and preventing the baffle plate from directly coming into contact with the hollow fiber membrane bundle. In Japanese Patent Application Laid-open No. 2000-350781, in order to prevent the hollow fiber membrane from breaking due to adhesion with the baffle plate during manufacture (i.e. potting step), the baffle plate is formed to have such a length that the ends of the baffle plate reaches a resin layer formed on each end of the hollow fiber membrane bundle. In these technologies, the shape and size of the tongue-shaped baffle plate, formed to have a curvature almost along the inner circumferential surface in the tubular housing at an interval from the inner circumferential surface at positions corresponding to the treatment liquid inlet and outlet on the inner circumferential surface, are equal on the inlet side and the outlet side.

However, leakage due to breakage of the hollow fiber membrane also occurs due to impact caused by dropping which accidentally occurs during transportation or handling of the hollow fiber membrane module, in addition to the case where impact occurs on the hollow fiber membrane due to a water stream when the treatment liquid enters through the treatment liquid inlet or is discharged through the treatment liquid outlet. Either baffle plate as described above exhibits an excellent effect on reduction of impact due to entrance or discharge of the treatment liquid, but does not exhibit an effect of preventing occurrence of leakage due to dropping impact and the like when handling the hollow fiber membrane module. Japanese Patent Application Laid-open No. 2003-102833, for example, discloses a rim-type dispersion ring (synonymous with baffle plate) which holds the entire periphery of the hollow fiber membrane bundle and is formed along a urethane surface which is curved by centrifugal molding in order to prevent the hollow fiber membrane from breaking due to high speed water stream washing when re using the dialyzer. Such a peripheral type baffle plate is preferable from the viewpoint of protecting the entire end portion of the hollow fiber membrane bundle. However, since it is difficult to provide the baffle plate formed along the curve of the urethane surface and mold the module, this technology involves difficulty in production.

As described above, the approach concerning the hollow fiber membrane and the housing shape in order to prevent breakage of the end portion of the hollow fiber membrane has a specific problem, and the effect is not necessarily satisfactory. Therefore, the hollow fiber membrane type fluid treatment device is still unsatisfactory from the viewpoint of improvement of the substance removal performance and/or prevention of breakage of the membrane. In particular, room for improvement is still left as to the structure and shape of the housing in comparison with the approach to the hollow fiber membrane (bundle) which has been widely studied by increasing the strength or providing with the spacer, crimp, or the like.

DISCLOSURE OF THE INVENTION

An object of the present invention is to improve the substance removal performance of a hollow fiber membrane type fluid treatment device having a tubular housing containing a hollow fiber membrane bundle by causing a fluid such as a dialysate to uniformly flow between the hollow fiber membranes by an approach completely differing from the conventional approach. More preferably, an object of the present invention is to provide a hollow fiber membrane type fluid treatment device excellent in effectively preventing occurrence of breakage of the end portion of the hollow fiber membrane caused by impact due to dropping or a water stream.

In order to achieve the above object, the inventors of the present invention have conducted extensive studies about the shape of the housing of the hollow fiber membrane type fluid treatment device. As a result, the inventors have found that the substance removal performance is significantly improved and the variation in the substance removal performance is reduced by providing a portion which gradually increases in diameter toward the end face of the housing on at least the treatment liquid inlet side in the tubular housing. The inventors have also found that occurrence of leakage due to breakage of the hollow fiber membrane is significantly reduced depending on the diameter-expanding portion. These findings have led to the completion of the present invention.

Specifically, the present invention relates to a hollow fiber membrane type fluid treatment device comprising at least a body portion of tubular housing containing a hollow fiber membrane bundle; a housing head portion which is connected with one end of the housing body portion and has a resin layer where the hollow fiber membrane bundle is fixed by using a resin composition, and a connection port which serves as a treatment liquid inlet; a housing head portion which is connected with the other end of the housing body portion and has a resin layer where the hollow fiber membrane bundle is fixed by using a resin composition, and a connection port which serves as a treatment liquid outlet; header caps attached to these housing head portions and having a treatment target liquid connection ports, respectively; characterized in that the fluid treatment device has at least a diameter-expanding portion which is provided to an inner surface of a treatment liquid inlet side in the tubular housing and enables the hollow fiber membranes to be disposed so that a distance between the hollow fiber membranes is gradually increased toward an end face of the treatment liquid inlet side.

The present invention also relates to the hollow fiber membrane type fluid treatment device, wherein the diameter-expanding portion comprises a baffle plate provided at a position corresponding to the treatment liquid inlet of the tubular housing and interspactially from an inner circumference of the tubular housing over the entire inner circumference at a curvature almost along the inner circumference, and the baffle plate gradually increases in diameter toward the end face of the housing.

The present invention relates to the hollow fiber membrane type fluid treatment device, wherein the diameter-expanding portion comprises an end tapered portion which increases in diameter toward the end face of the housing body portion; and the inner surface of the housing body portion on the treatment liquid inlet side has a body straight portion.

According to the hollow fiber membrane type fluid treatment device of the present invention, when the hollow fiber membrane type fluid treatment device is used as a hemodialyzer, since a dialysate which has entered from the treatment liquid inlet flows into inside the hollow fiber membrane bundle and uniformly flows between the hollow fiber membranes, the substance removal performance of the hemodialyzer is significantly improved. Moreover, breakage of the end portion of the hollow fiber membrane caused by impact due to dropping or a water stream can be very effectively prevented. The hollow fiber membrane type fluid treatment device of the present invention can be also used as an external pressure type filtration device such as an endotoxin cut filter. Specifically, since the flow of the treatment liquid inside the housing is made uniform between the hollow fiber membranes, the substance removal performance is improved, whereby an excellent separation function can be achieved.

BEST MODE FOR CARRYING OUT THE INVENTION

The present invention is described below in detail.

The following description illustrates an example in which the fluid is blood and the fluid treatment device is a hemodialyzer. However, the hollow fiber membrane type fluid treatment device of the present invention is not limited to the hemodialyzer, and may be used in various fields such as the medical treatment field, food field, and industrial field.

Figure 1:
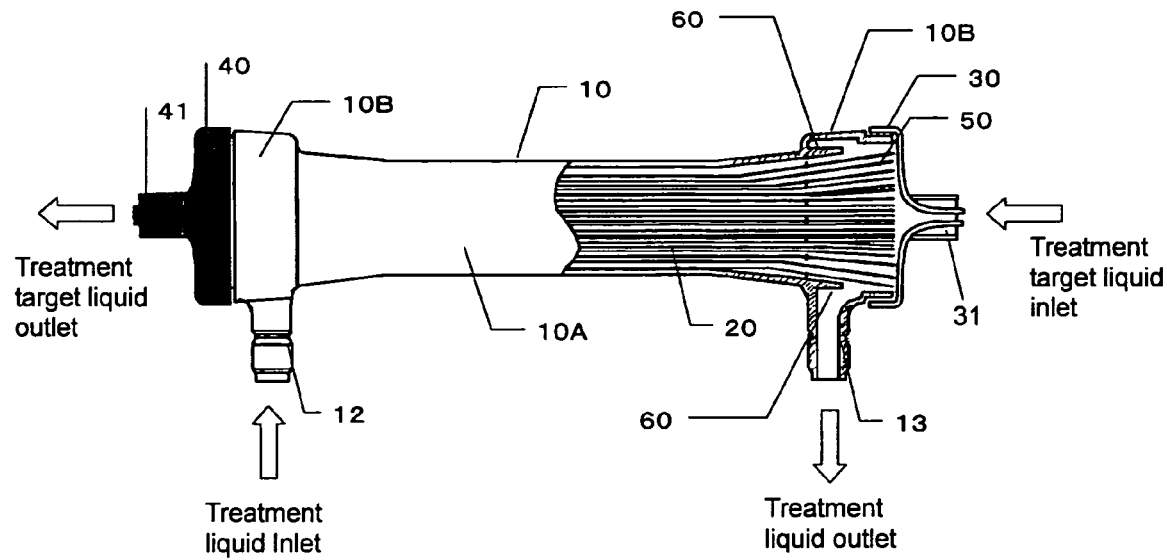
FIG. 1 is a partial cross-sectional front schematic diagram showing an example of a hollow fiber membrane type fluid treatment device of the present invention.

FIG. 1 is a partial cross-sectional front schematic diagram of the hollow fiber membrane type fluid treatment device showing an example of one embodiment of the present invention.

The hollow fiber membrane type fluid treatment device according to the embodiment may be used as a hemodialyzer, and includes a tubular housing 10 including a body portion 10A containing a hollow fiber membrane bundle 20, in which several hundred to several thousand hollow fiber membranes are bundled, and head portions 10B connected with the body portion 10A, and header caps 30 and 40 attached to both ends of the tubular housing 10, respectively. Treatment liquid connection ports 12 and 13 are formed in the head portions 10B of the tubular housing 10. The treatment liquid connection port 12 serves as a inlet of dialysate, and the treatment liquid connection port 13 serves as a outlet of the treatment liquid, for example. The header cap 30 is provided with a supply port 31 of a treatment target liquid such as blood, and the header cap 40 is provided with a discharge port 41 of the treatment target liquid, for example.

The mechanism by which blood is purified through the dialyzer is described below. Blood which has entered through the supply port 31 flows into inside the hollow fiber membranes from the open end of the hollow fiber membrane. The blood then runs through inside of each membrane, flows out from the other open end, and is discharged through the discharge port 41. The treatment liquid such as dialysate flows into the tubular housing through the treatment liquid connection port 12, runs through between thousands of hollow fiber membranes arranged in the body portion, and is discharged through the treatment liquid connection port 13. These fluids exchange substances through the hollow fiber membranes during flowing through the tubular housing.

Each end of the hollow fiber membrane bundle 20 is fixed to the inside of the housing by using a resin layer 50 formed of a resin composition (potting material) such as urethane. While the treatment target liquid flows inside each hollow fiber membrane, the treatment liquid flows along the outer surface of each hollow fiber membrane, so that wastes in the blood are removed through dialysis utilizing a diffusion phenomenon due to concentration gradient through the hollow fiber membrane bundle 20 or filtration due to pressure gradient.

In the hollow fiber membrane type fluid treatment device of the present invention, a portion which gradually increases in diameter toward the end face of the housing is provided on at least the treatment liquid inlet side in the tubular housing. Specifically, the portion is a baffle plate internally provided near the treatment liquid connection port or a tapered portion provided in the housing body portion.

Figure 2:
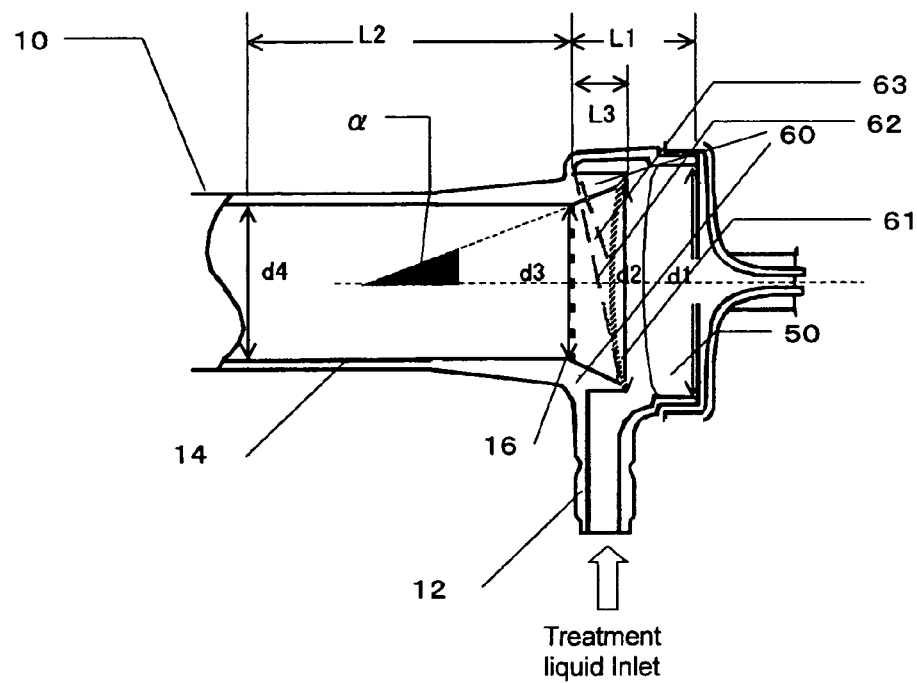
FIG. 2 is an enlarged schematic diagram of the vicinity of a treatment liquid inlet shown in FIG. 1 for illustrating an example of a baffle plate of the present invention.
Figure 3:
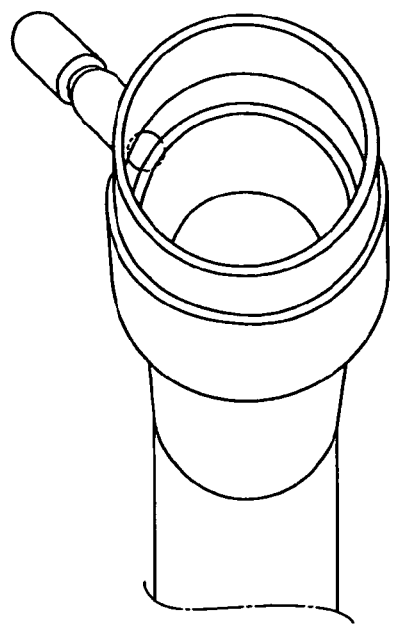
FIG. 3 is a stereoscopic schematic diagram showing the shape of the baffle plate.

FIG. 2 is an enlarged schematic diagram of one side of FIG. 1 for illustrating an example of the baffle plate. Moreover, FIG. 3 shows a stereoscopic schematic diagram of the baffle plate.

In FIG. 2, the length of the head portion 10B is defined as L1, the half length of the body portion 10A is defined as L2, the height of a baffle plate 60 which is connected with an inner surface 14 of the body portion and gradually increases in inner diameter toward the end face of the housing body portion is defined as L3, the inner diameter of the inner surface 14 of the body portion 10A is defined as d4, the inner diameter of a joint portion 16 connecting the body portion 10A and the head portion 10B is defined as d3, the inner diameter of the end of the baffle plate 60 is defined as d2, and the diameter of the hollow fiber membrane bundle 20 at the end face of the resin layer 50 is defined as d1.

As shown in FIG. 2, the inner surface of the tubular housing 10 expands to the inner surface 14 of the body portion and the baffle plate 60 which is connected with the inner surface 14 and increases in inner diameter toward the end face of the housing body portion. Since the baffle plate 60 has such a shape, the hollow fiber membrane bundle is easily arranged along the inclined inner surface of the baffle plate 60 so that the distance between the hollow fiber membranes is gradually increased toward the end face on the treatment liquid inlet side. Specifically, the hollow fiber membrane bundle 20 is uniformly dispersed along the inclined inner surface of the baffle plate 60 so that the hollow fiber membranes are uniformly arranged without causing a large space to be formed between the hollow fiber membranes in the housing head portion 10B. As a result, when the dialysate as the treatment liquid enters through the treatment liquid connection port 12, the dialysate penetrates inside the hollow fiber membrane bundle 20 so that the dialysate tends to uniformly flow between the hollow fiber membranes. This increases the substantial area of the hollow fiber membrane coming into contact with the dialysate, whereby the removal performance of blood wastes through the hollow fiber membrane bundle 20 is significantly improved. Moreover, breakage of the end portion of the hollow fiber membrane caused by impact due to accidental dropping during transportation or impact due to fluid can be effectively prevented. The hollow fiber membrane bundle 20 may not be increased in diameter along the increased diameter of the baffle plate, and may be linear along the center axis direction of the housing. In this case, a small interspace tends to form between the hollow fiber membranes near the inlet due to the flow of the treatment liquid entering from the inlet side. However, since vibration of the hollow fiber membrane is properly prevented by the baffle plate provided in the circumferential direction, breakage of the membrane rarely occurs.

As another effect, since the hollow fiber membranes constituting the hollow fiber membrane bundle 20 are uniformly dispersed in the housing head portion 10B due to the presence of the tapered portion of the baffle plate 60, s impact load due to dropping or a water stream is not locally charged only to the portion of the hollow fiber membrane bundle. Therefore, breakage of the hollow fiber membrane can be effectively prevented.

In the present invention, the baffle plate is formed over the entire inner circumference of the housing. However, an interspace may be formed in the circumferential direction by providing a slit or a small hole such as a punching plate, for example. In this case, breakage of the end portion of the hollow fiber membrane caused by impact due to accidental dropping during transportation or impact due to fluid can also be prevented. Moreover, since the dialysate penetrates inside the hollow fiber membrane bundle 20 due to the presence of the tapered portion of the baffle plate so that the dialysate uniformly flows between the hollow fiber membranes, the removal performance of blood wastes is significantly improved.

The substance removal performance and the membrane damage prevention effect can be obtained by providing the baffle plate on at least the treatment liquid inlet side. However, it is more preferable to provide the baffle plate on each of the inlet side and the outlet side particularly from the viewpoint of the damage prevention effect.

As to the inclination of the baffle plate, the angle $\alpha$ formed by the centerline of the inner surface of the housing body portion and the inner-surface of the baffle plate is defined by the following equation (1).

$$\alpha = \tan^{-1}\{1/2 \cdot (d2-d3)/L3\} \quad (1)$$

Specifically, the angle $\alpha$ is a value which numerically indicates the ratio of change in the diameter of the inner surface of the baffle plate which gradually increases in diameter toward the end face of the housing body portion. The angle $\alpha$ significantly affects occurrence of breakage of the end portion of the hollow fiber membrane.

It is preferable that the angle $\alpha$ formed by the centerline of the inner surface of the housing body portion and the inner surface of the baffle plate be greater than 0° and smaller than $\tan^{-1}\{1/2 \cdot (d1-d3)/L3\}$.

If the angle $\alpha$ is 0°, that is, the baffle plate is parallel to the centerline of the inner surface of the housing body portion, since the hollow fiber membrane coming into contact with the end face of the baffle plate is in the status of being loaded, the hollow fiber membrane may be damaged in the contact area due to impact caused by dropping or a water stream, whereby leakage tends to occur. Similarly, if the angle $\alpha$ is smaller than 0°, since the hollow fiber membrane bundle is compressed by the baffle plate, the hollow fiber membrane may be damaged in that area due to impact caused by dropping or a water stream, whereby leakage tends to occur. Moreover, since any interspace is not formed between the inner circumferential surface of the baffle plate and the hollow fiber membrane bundle at all, particularly when the bundle is linear without being increased in diameter, any space is rarely formed between the hollow fiber membranes, even when the treatment liquid enters through the treatment liquid inlet, whereby a uniform flow may not be obtained.

If the angle $\alpha$ is greater than $\tan^{-1}\{1/2 \cdot (d1-d3)/L3\}$, since an interspace is formed between the hollow fiber membrane bundle 20 and the baffle plate 60, the hollow fiber membranes are not uniformly dispersed and a large space is also formed between the hollow fiber membranes. As a result, the hollow fiber membranes may be damaged in that area due to impact caused by dropping or a water stream, whereby leakage tends to occur.

The angle $\alpha$ is preferably 1° or more, and particularly preferably 3° or more.

The flow rate of the treatment liquid differs depending on the purpose of use. In order to increase the removal performance of blood wastes by obtaining a uniform flow even at a low flow rate or to increase the removal performance at a high flow rate, it is preferable that the angle $\alpha$ be greater than 1° and smaller than $2/3 \cdot \tan^{-1}\{1/2 \cdot (d1-d3)/L3\}$, and it is particularly preferable that the angle $\alpha$ be greater than 3° and smaller than $2/3 \cdot \tan^{-1}\{1/2 \cdot (d1-d3)/L3\}$.

The height L3 of the baffle plate is preferably 2 to 12 mm, and still more preferably 5 to 10 mm. If the height of the baffle plate is too low, breakage of the hollow fiber membrane due to impact caused by dropping or a water stream may not be prevented. If the height of the baffle plate is too high, since the distance between the baffle plate 60 and the resin layer become narrower, the treatment liquid which has entered through the treatment liquid inlet 12 does not sufficiently flow into the hollow fiber membrane bundle 20.

FIG. 2 illustrates an example in which the inner surface 14 of the body portion and the inner surface of the baffle plate 60 are linearly inclined. However, these inclinations may not be limited to linear shape but may be shape with curvature. The inner surface may be a combination of plural inclinations of two or more shapes. For example, the inner surface may be formed in two stages combined a tapered surface with a large angle and another tapered surface with a small angle.

In FIG. 2, the shape of the edge of the baffle plate is preferably used not only in the case of being identical over the entire inner circumference of the housing, but also in the case of being curved corresponding to the outer circumference of the resin layer 50, as indicated by 61. This is an example in which the shape of the edge of the baffle plate is curved along the outer circumference of the resin layer. Specifically, the height (L3) of the baffle plate differs in the circumferential direction of the baffle plate (broken lines 61 in FIG. 2 are lines which do not appear in the cross-sectional diagram). This allows the distance between the resin layer 50 and the end of the baffle plate 60 to be maintained almost constant over the entire inner circumference of the housing. Therefore, since the treatment liquid which has entered through the treatment liquid connection port 12 flows along the outer circumference of the baffle plate 60 and uniformly penetrates into the hollow fiber membrane bundle 20, an excellent removal performance is obtained.

Similarly, the shape of the edge of the baffle plate, in particular, the height (L3) of the baffle plate may differ between the vicinity of the treatment liquid connection port and the vicinity of the portion opposite to the treatment liquid connection port in the circumferential direction (broken lines 62 or 63 in FIG. 2).

The above-described baffle plate may be formed by using an arbitrary known method, such as a method of welding the baffle plate to the body portion of the tubular housing, or a method of forming the baffle plate integrally with the inner surface of the tubular housing by injection molding, but not limited thereto.

The tapered end portion of the housing body portion is described below.

Figure 4:
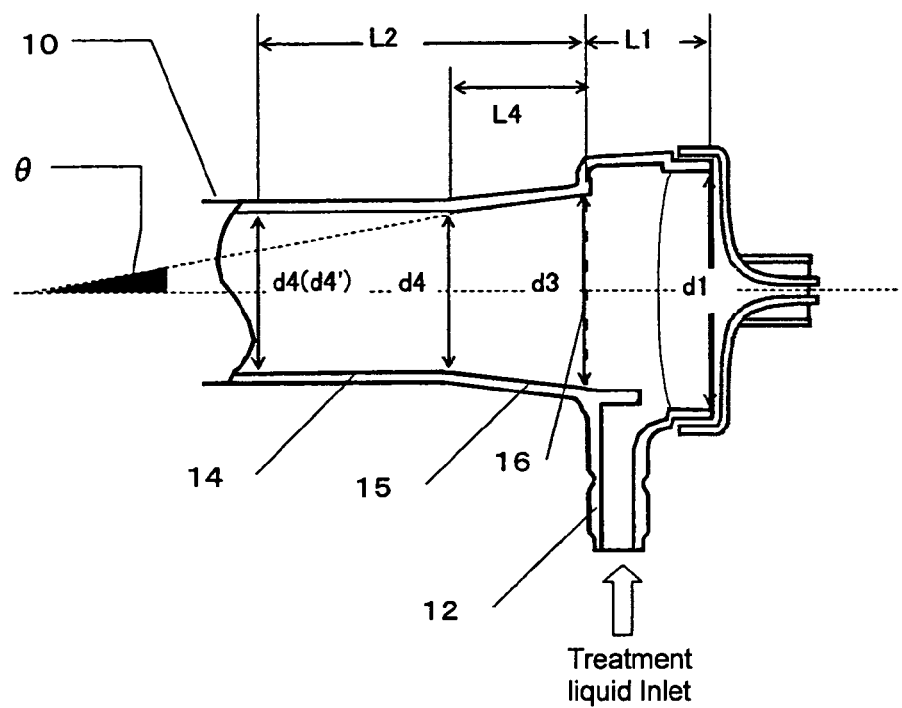
FIG. 4 is an enlarged schematic diagram of the vicinity of a treatment liquid inlet shown in FIG. 1 for illustrating an example of an end tapered portion of the present invention.

FIG. 4 is an enlarged schematic diagram of one side of the tubular housing 10 shown in FIG. 1 for illustrating a tapered portion.

In FIG. 4, the length of the head portion 10B is defined as L1, the half length of the body portion 10A is defined as L2, the length of an end tapered portion 15 (one side) which increases in diameter toward the end face of the housing body portion is defined as L4, the inner diameter of the inner surface straight portion 14 of the body portion 10A is defined as d4, the inner diameter of the joint portion 16 between the body portion 10A and the head portion 10B is defined as d3, and the diameter of the hollow fiber membrane bundle 20 at the end face of the resin layer 50 is defined as d1.

As shown in FIG. 4, the portion corresponding to the half length of the body portion 10A of the tubular housing 10 comprises the straight portion 14 in which the inner surface of the body portion is parallel to the centerline of the inner surface of the housing body portion, and the tapered portion 15 which is connected with the straight portion 14 and its inner surface gradually increases in diameter toward the end face of the housing body portion. Specifically, the straight portion refers to the portion 14 which is parallel to the centerline of the inner surface of the housing body portion in the inner surface of the body portion 10A of the tubular housing.

In FIG. 4, the length of the straight portion is (L2−L4), and the inner diameters of the housing at both ends of the straight portion are equally d4. The tapered portion refers to the portion 15 which is connected with the straight portion and gradually increases in diameter toward the end face of the housing body portion. In FIG. 4, the length of the tapered portion is L4, and the inner diameters of the housing at both ends of the tapered portion is differently d4 and d3 (d4<d3). These constructions significantly improves the substance removal performance of the hemodialyzer.

Specifically, for example, when the dialysate as the treatment liquid flows into the housing through the treatment liquid connection port 12, since the hollow fiber membrane bundle 20 in which several thousand hollow fiber membranes are bundled is uniformly increased in diameter along the tapered portion 15, a space is formed between the hollow fiber membranes. Therefore, the dialysate reaches to the center of the hollow fiber membrane bundle 20 and uniformly flows between the hollow fiber membranes with ease. Specifically, the dialysate can uniformly come in contact with not only the outer surfaces of the hollow fiber membranes at the bundle outer side, but also the outer circumferential surfaces of all hollow fiber membranes in the area from the center to outer side of the hollow fiber membrane bundle. Therefore, since the surface area of the hollow fiber membrane coming in contact with the dialysate is substantially increased, the removal performance of blood wastes through the hollow fiber membrane bundle 20 is thought to be improved significantly.

Moreover, since the straight portion 14 has a fiber density, which indicates the density of the hollow fiber membranes inside the housing, higher than that of the end tapered portion 15, the flow rate of the dialysate which has uniformly flowed into the hollow fiber membrane bundle 20 in the tapered portion is higher in the straight portion than in the tapered portion, therefore the mass transfer coefficient in the dialysate is increased, whereby waste removal is promoted.

Furthermore, since the hollow fiber membranes are fixed by the resin layer 50 so that the hollow fiber membrane bundle is uniformly increased in diameter along the end tapered portion 15, the hollow fiber membranes which constitutes the hollow fiber membrane bundle 20 are uniformly dispersed in the housing head portion 10B. Therefore, since a large space is not formed between the hollow fiber membranes in the housing head portion 10B, leakage of the treatment target liquid such as blood, caused by breakage of the hollow fiber membrane due to impact applied to the hollow fiber membrane during transportation of the product, rarely occurs. Those effects are also obtained.

The straight portion referred in the present invention not only includes the case where the inner surface of the housing body portion 10A is completely parallel to the centerline of the inner surface of the body portion, but also includes a minute taper called a "draft angle" as a substantially straight portion. The draft angle is usually 0.5° or less when a tubular housing with a length of about 30 to 50 cm is formed by injection molding. The inventors of the present invention have found that excellent substance removal performance cannot be obtained when the angle of the end tapered portion of the housing body portion is less than 0.5°. Therefore, in the present invention, a portion having an angle of 0.5° or less is substantially classified as the straight portion.

The effect of improving the substance removal performance can be obtained by providing the end tapered portion and the straight portion at least on the treatment liquid inlet side in the inner surface of the housing body portion. However, the end tapered portion and the straight portion may be provided on both the inlet side and the outlet side. In this case, the angle and the shape of the tapered portion and the length of the straight portion may differ between the inlet side and the outlet side, that is, the housing may be unsymmetrical.

Regarding the inclination of the end tapered portion in housing body portion, an angle θ formed by the centerline of the inner surface of the housing body portion and the inner surface of the end tapered portion is defined by the following equation (2).

$$\theta = \tan^{-1}\{1/2 \cdot (d3-d4)/L4\} \quad (2)$$

Specifically, the angle θ is a value indicating the ratio of change in the diameter of the inner surface 15 of the end tapered portion which gradually increases in diameter toward the end face of the housing body portion. The angle θ significantly affects the removal performance of waste of the hemodialyzer. Specifically, it is important that the angle θ formed by the centerline of the inner surface of the housing body portion and the inner surface of the end tapered portion be greater than 0° and smaller than $\tan^{-1}\{1/2 \cdot (d1-d4)/L4\}$.

If the angle θ formed by the centerline of the inner surface of the housing body portion and the inner surface of the end tapered portion is not more than 0°, the dialysate may make a serious short-path, whereby the removal performance is significantly decreased. If the angle θ is only slightly greater than 0°, such a short-path does not occur. On the other hand, if the angle θ is greater than $\tan^{-1}\{1/2 \cdot (d1-d4)/L4\}$, a space is formed between the hollow fiber membrane bundle 20 and the end tapered portion 15 so that the dialysate makes a short-path through the space, whereby the removal performance is significantly decreased. It is still more preferable that the angle θ be greater than 0.58°.

The inlet flow rate of the treatment liquid differs depending on the purpose of use. In order to increase the removal performance of blood wastes by obtaining a uniform flow even at a low flow rate or to increase the removal performance at a high flow rate, it is preferable that the angle θ be greater than 0.58° and smaller than $2/3 \cdot \tan^{-1}\{1/2 \cdot (d1-d4)/L4\}$.

FIG. 4 illustrates an example in which the straight portion and the tapered portion are respectively formed in one stage. The number of stages of the tapered portion is not limited to one, but may be two or more. For example, it is possible for the tapered portion to be formed by a tapered portion with a large angle, a tapered portion with a small angle, and a straight portion in the order from the end face toward the body portion. In the case of forming a two-stage tapered portion, it is necessary that the angle of either or all the tapered portions be within the above range. In the case of forming a two-stage tapered portion, if the angle of the tapered portion at a small angle is not more than 0.5°, the tapered portion is considered to be a straight portion, and the tapered portion is classified as a one-stage tapered portion.

The tapered portion used herein is not limited to a linear tapered portion, and includes a tapered portion having a certain curvature. Specifically, a tubular body portion which the cross-sectional area is continuously increased toward the inlet end portion is also included within the scope of the present invention. In FIG. 4, as to the straight portion of the housing body portion, it is preferable that the ratio ((L2−L4)/L4) of the length of the body straight portion to the length of the end tapered portion be 0.7 to 20. If the ratio of the length of the straight portion to the length of the end tapered portion is smaller than 0.7, a slight short-path of the dialysate may occur, whereby the removal performance may be insufficient. If the ratio is greater than 20, since the length of the end tapered portion in comparison with the length of the straight portion may be short, a short-path may also occur.

It is important that the ratio (d3/d4) of the inner diameter of the end tapered portion on the end face side to the inner diameter of the straight portion of the body portion is more than 1 and not more than 3. If the ratio of the inner diameter of the end tapered portion on the end face side to the inner diameter of the straight portion of the body portion is less than 1, since the spaces between the hollow fiber membranes is small, the permeability of the dialysate into the hollow fiber membrane bundle extremely deteriorates. If the ratio is more than 3, since the hollow fiber membrane bundle 20 is largely curved at the joint surface d3 between the housing body portion 10A and the housing head portion 10B in view of the manufacturing method of the body fluid treatment device, the hollow fiber membranes are not uniformly dispersed in the housing head portion 10B.

When the housing body portion does not have a complete straight portion in the inside, the minimum diameter (d4') of the body portion may be alternatively used for the inner diameter (d4) of the straight portion.

Figure 6:
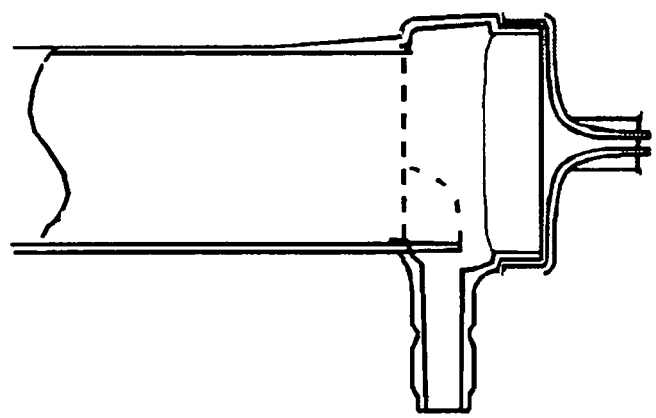
FIG. 6 is an enlarged schematic diagram of the vicinity of a treatment liquid inlet side for illustrating an example of conventional technology in which no end tapered portion is included.

As described above, it is important that the housing body portion has the end tapered portion and the straight portion on the inner surface. In the case where the entire inner surface of the body portion is formed only of the straight portion as shown in FIG. 6, the dialysate undergoes a short-path phenomenon, whereby the removal performance of blood wastes is extremely decreased. The short-path phenomenon used herein refers to a phenomenon in which the dialysate enters through the inlet, is immediately discharged through the outlet along the outer circumference of the hollow fiber membrane bundle 20, and thus does not substantially enter into the hollow fiber membrane bundle 20.

On the other hand, in the case where the diameter is reduced depending on a predetermined taper from the end portion of the treatment liquid inlet to the vicinity of the middle of the body portion, becomes minimum in the vicinity of the middle, and is increased depending on a predetermined taper from the vicinity of the middle toward the treatment liquid outlet, the effect of improving the substance removal performance is obtained. In this case, a straight portion having an inner circumferential surface parallel to the centerline does not substantially exist. However, since the hollow fiber membranes are dispersed over a wide space depending on the taper with a certain angle, the treatment liquid flows to the space and enters into the hollow fiber membrane bundle, and the flow rate of the treatment liquid is increased in accordance with the diameter of the inner circumferential surface which is gradually reduced, whereby the substance exchange with the blood inside the hollow fiber membrane is thought to be promoted. In this case, the effect cannot be obtained at a minute angle as small as a draft angle, it is thus preferable that the angle θ of the end tapered portion be at least 0.5° or more.

The manufacturing method of above-described housing (body portion) provided with the end tapered portion is not particularly limited, but the housing may be formed by using a known method, such as a method of attaching the end tapered portion and the housing head portion to the end portion of a straight pipe, or a method of integrally forming by adjusting the blanking condition of the injection molding. In FIGS. 1 and 4, the thickness of the housing is almost constant and the shape of the housing is inclined. However, the present invention is not limited thereto. The outer diameter of the housing may not be changed and the inner surface of the housing may be tapered by changing the thickness of the housing.

Hereinbefore, the baffle plate and the end tapered portion of the inner surface of the housing body portion are separately described as a portion which is provided at least on the treatment liquid inlet side of the tubular housing and gradually increases in diameter toward the end face of the housing. Although those individually exert an effect as described above, a more excellent effect can be obtained on the substance removal performance and the breakage prevention of hollow fiber membrane by using the baffle plate and the end tapered portion in combination. The combination is not particularly limited. For example, when providing the baffle plate and the end tapered portion of the present invention on the treatment liquid inlet side, the outlet side may be provided with only the baffle plate, only the end tapered portion, both the baffle plate and the end tapered portion, or none of these. When using the baffle plate and the end tapered portion in combination, it is preferable that each of the inclination angles $\alpha$ and $\theta$ be within the above-described preferable range. It is still more preferable that the inclination angles $\alpha$ and $\theta$ be the same and the baffle plate and the inner surface of the end tapered portion are continuously inclined (flush surface shape).

In the hollow fiber membrane type fluid treatment device of the present invention, the shape of the housing is important. The hollow fiber membrane placed in the housing is not particularly limited. A hollow fiber membrane which may be used for dialysis, filtration, adsorption, or the like may be used without specific limitations. As the material for the hollow fiber membrane, for example, cellulose polymers such as regenerated cellulose and cellulose acetate, synthetic polymers such as polyacrylonitrile, polysulfone, polyethersulfone, polyvinylidene fluoride, polyethylene, polyester, polyamide, ethylene-vinyl alcohol copolymer, and a polyester-polyethersulfone polymer alloy, and the like can be given.

In the field of hemodialysis particularly, a hydrophilized polysulfone hollow fiber membrane has been widely used as the material exhibiting excellent removal performance for substances ranging from a low-molecular-weight protein to a low-molecular-weight component such as urea. A lot of manufacturing methods for the hydrophilized polysulfone hollow fiber membrane have been disclosed. For example, WO 98/52683 discloses a hydrophilized polysulfone hollow fiber membrane having an inner diameter of 200 μm, a thickness of 45 μm, and a water permeablity of 160 to 220 ml/m$^2$·hr·mmHg. The hollow fiber membrane type fluid treatment device of the present invention is obtained by placing a hollow fiber membrane bundle, formed by bundling about 9000 to 10000 hollow fiber membranes, in a tubular housing provided with a specific baffle plate and/or end tapered portion, and fixing the ends of the hollow fiber membranes to the housing by filling with a potting material, followed by assembling. According to such a hollow fiber membrane type fluid treatment device, a urea clearance of about 186 to 200 ml/min and a vitamin B12 clearance of about 130 to 170 ml/min as a substance removal performance are obtained. In a more preferable embodiment, such high performance as a urea clearance of about 195 to 200 ml/min and a vitamin B12 clearance of about 140 to 170 ml/min can be achieved. Moreover, the variation in clearance is small when measuring the clearance using a plurality of fluid treatment devices, as shown in the following examples.

An endotoxin cut filter is obtained by using a hollow fiber membrane made of a polysulfone polymer or a polyester-polyethersulfone polymer alloy to which a hydrophilizing agent is not added, for example. A highly water permeable filter is obtained by using a polysulfone hollow fiber membrane. When introducing the treatment target liquid through the treatment liquid inlet 12 and discharging the treatment liquid from inside of the hollow fiber membranes, the treatment target liquid is easily and uniformly filtered through each hollow fiber membrane, whereby an excellent removal performance and filtration performance may be obtained.

The hollow fiber membrane type fluid treatment device of the present invention may be used for such various applications. Since the hollow fiber membrane type fluid treatment device has a particularly significant effect on improvement of the substance removal performance by utilizing diffusion, the hollow fiber membrane type fluid treatment device may be most suitably used as a hemodialyzer.

EXAMPLES

The present invention is described below in detail by way of examples and comparative examples. However, the present invention is not limited to the following examples. The measurement method and the evaluation method used in the present invention are firstly described below.
(Urea and Vitamin B12 Clearances)

The removal performance of blood wastes was evaluated by using the clearances of urea (molecular weight: 60), which are typical uremia substances, and vitamin B12 (molecular weight: 1,355) as indices. The measurement was carried out according to the performance evaluation standard provided by the Japanese Society for Artificial Organs by using a hemodialyzer module under the condition of a blood flow rate of 200 mL/min, a dialysate flow rate of 500 mL/min, and a transmembrane pressure (TMP) of 0 mmHg. The clearance was calculated from the concentration of urea or vitamin B12 on the blood inlet side (CBin) and the concentration of urea or vitamin B12 on the outlet side (CBout) by using the following equation. In the measurement, three hollow fiber membrane type fluid treatment devices taken out at random were subjected to the clearance measurement, and the average value and the standard deviation were calculated.

$$\text{Clearance} = 200 \times (C\text{Bin} - C\text{Bout})/C\text{Bin} \quad (3)$$

The unit of the resulting value is "ml/min", which indicates the amount of wastes removed from the fluid of blood side. The larger the value, the higher the removal performance of blood wastes of the hemodialyzer.
(Drop Impact Test)

2 ml of sterilized water was respectively removed from the treatment liquid connection ports 12 and 13 of the hollow fiber membrane type fluid treatment module as shown in FIG. 1, and the module was caused to drop onto a concrete floor from a height of 30 cm in the direction in which the treatment target liquid outlet faces downward. After repeating this operation five times, the presence or absence of leakage was confirmed by performing an underwater pressure loading test. This procedure was repeated until the module was dropped 50 times in total.

The underwater pressure loading test is described below. The hollow fiber membrane type fluid treatment module is immersed in water in a state in which the treatment target liquid outlet 41 is sealed with a plug and the treatment liquid inlet 12 and the treatment liquid outlet 13 are open, and then the hollow fiber membrane type fluid treatment module is held for 30 seconds in a state in which air is introduced through the treatment target liquid inlet 31 at a pressure of 1.5 kgf/cm$^2$. It is judged that leakage occurred if air leaked from the treatment target liquid side to the treatment liquid side, and it is judged that leakage did not occur if air did not leak from the treatment target liquid side to the treatment liquid side.

This operation was performed for ten modules, and the number of modules in which leakage occurred was taken as the leakage occurrence rate.

(Dialysate Flowability Test)

The dialysate flowability was evaluated by using the following method. The dialysate was caused to flow through the dialysate side at a flow rate of 500 ml/min. 1 shot 2 ml of Red india ink was injected through the dialysate inlet together with the dialysate, and the dialysate discharged was sampled every 10 ml. The absorbance of the dialysate, that is, the red india ink concentration in the dialysate was then measured. The resulting absorbance was plotted in a graph for every fraction, and the dialysate flowability was evaluated from the degree of deviation of the absorbance. The shape of the graph close to the normal distribution without deviation is an ideal flow (plug flow) which allows the dialysate to uniformly penetrate the hollow fiber membrane bundle.

Example 1

A hollow fiber membrane bundle was formed by bundling 9200 hydrophilized polysulfone hollow fiber membranes (inner diameter: 200 μm, thickness: 45 μm, water permeablity: 300 ml/m²·hr·mmHg, aqueous mass transfer coefficient of urea: $9.0 \times 10^{-4}$ cm/sec, aqueous mass transfer coefficient of vitamin B 12: $3.1 \times 10^{-4}$ cm/sec) obtained from polysulfone and polyvinylpyrrolidone by using a known wet spinning method. The hollow fiber membrane bundle was placed in a tubular housing so that the membrane area might be 1.5 m². Both ends of the hollow fiber membrane bundle was potted with polyurethane resin to form a hollow fiber membrane type fluid treatment device. The inclination angle α of the baffle plate of the housing was made into 11.9°. The remainder of the above-defined values is also collectively shown in Table 1.

The clearance and the drop leakage occurrence rate of the resulting hollow fiber membrane type fluid treatment device are shown in Table 1.

Example 2

A hollow fiber membrane type fluid treatment device having a membrane area of 1.5 m² was formed in the same manner as in Example 1, except for using a baffle plate having the angle α of 11.9° and an edge curving along the outer circumference inside the resin layer as indicated by 61 shown in FIG. 2. In this case, since the height L3 of the baffle plate and the inner diameter d2 at the edge are not constant in the circumferential direction of the housing, data shown in the table is given as a reference value.

The clearance and the drop leakage occurrence rate of the resulting hollow fiber membrane type fluid treatment device are shown in Table 1.

Example 3

A hollow fiber membrane type fluid treatment device having a membrane area of 1.5 m² was formed in the same manner as in Example 1 except for using a tubular housing having an angle α of 1.2°. The clearance and the drop leakage occurrence rate of the resulting hollow fiber membrane type fluid treatment device are shown in Table 1.

Example 4

A hollow fiber membrane type fluid treatment device having a membrane area of 1.5 m² was formed in the same manner as in Example 1 except for using a tubular housing having an angle α of 3.3°. The clearance and the drop leakage occurrence rate of the resulting hollow fiber membrane type fluid treatment device are shown in Table 1.

Example 5

A hollow fiber membrane type fluid treatment device having a membrane area of 1.5 m² was formed in the same manner as in Example 1 except for using a tubular housing having an angle α of 13.6° and a completely straight body portion. The clearance and the drop leakage occurrence rate of the resulting hollow fiber membrane type fluid treatment device are shown in Table 1.

Comparative Example 1

A hollow fiber membrane type fluid treatment device having a membrane area of 1.5 m² was formed in the same manner as in Example 1 except for using a tubular housing having an angle α of 0° (i.e. baffle plate was parallel to the centerline of the inner surface of the housing body portion). The clearance and the drop leakage occurrence rate of the resulting hollow fiber membrane type fluid treatment device are shown in Table 1.

Comparative Example 2

Figure 5:
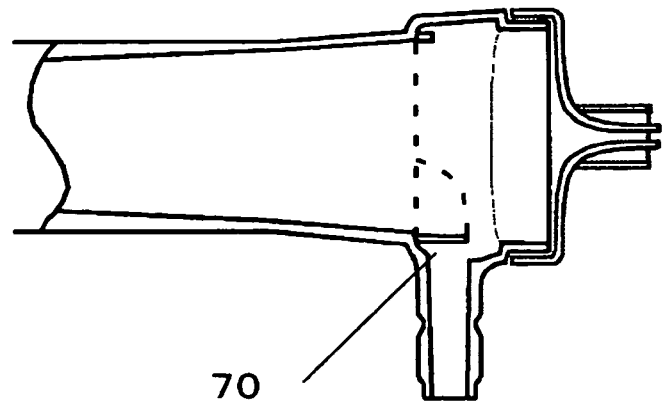
FIG. 5 is an enlarged schematic diagram of the vicinity of a treatment liquid inlet side for illustrating an example of conventional technology in which the entire housing body portion is formed only of a tapered portion.

A hollow fiber membrane type fluid treatment device having a membrane area of 1.5 m² was formed in the same manner as in Example 1 except for using a tubular housing provided with a tongue-shaped baffle plate 70 having a height of 9.5 mm and a width along the inner circumference of the body portion of 37 mm as shown in FIG. 5. The clearance and the drop leakage occurrence rate of the resulting hollow fiber membrane type fluid treatment device are shown in Table 1.

The urea clearances of Examples 1 to 5 were higher than those of Comparative Examples 1 and 2, and the variation in the urea clearance was also small. This suggests that the hollow fiber membrane type fluid treatment device of the present invention exhibits excellent removal performance of body fluid wastes. The drop leakage occurrence rates of Examples 1 to 5 were significantly lower than those of Comparative Examples 1 and 2. This suggests that the hollow fiber membrane type fluid treatment module of the present invention is a module ensuring excellent safety with a low leakage occurrence rate.

Example 6

Figure 7:
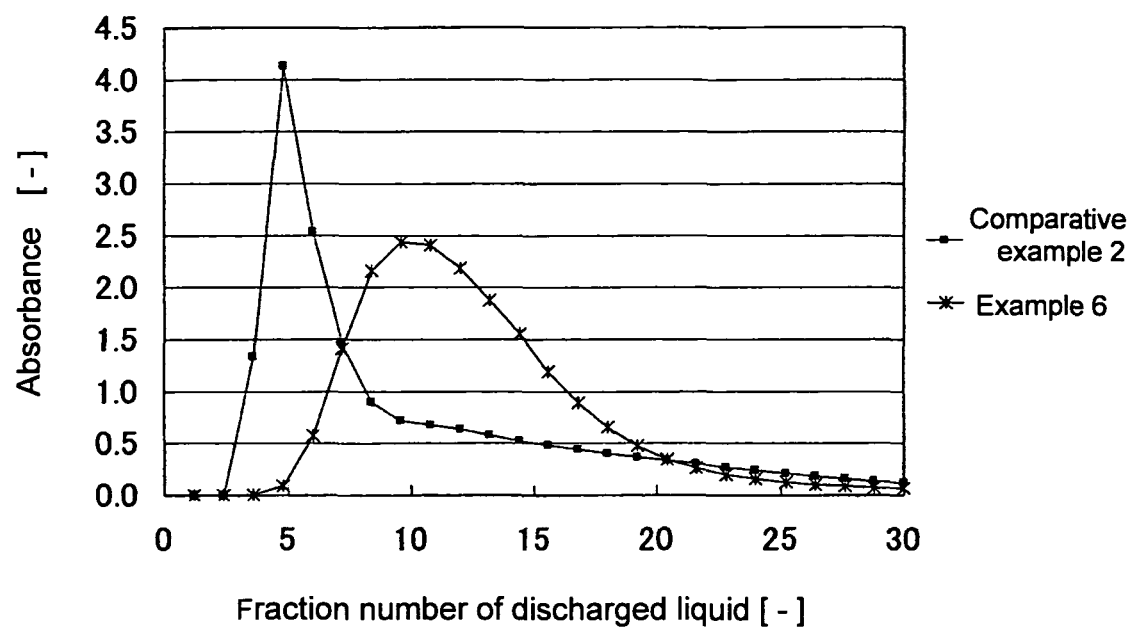
FIG. 7 is a graph showing the results of a dialysate flowability test using red india ink.

A hollow fiber membrane type fluid treatment device having a membrane area of 1.5 m² was formed in the same manner as in Example 1 except for using a tubular housing in which the length of the end tapered portion was 15 mm. The clearance of the resulting hollow fiber membrane type fluid treatment device is shown in Table 2. Results of the dialysate flowability test carried out using the same test specimen are shown in FIG. 7.

Example 7

A hollow fiber membrane type fluid treatment device was formed in the same manner as in Example 1 except for using a tubular housing in which the length of the end tapered portion was 11 mm and changing the membrane area to 1.7 m² by using 10,100 hollow fiber membranes. The clearance of the resulting hollow fiber membrane type fluid treatment device is shown in Table 2. The other values defined above are also shown in Table 2.

Example 8

A hollow fiber membrane type fluid treatment device was formed in the same manner as in Example 1 except for using a tubular housing in which the length of the end tapered portion was 70 mm and changing the membrane area to 1.7 m² by using 10,100 hollow fiber membranes. The clearance of the resulting hollow fiber membrane type fluid treatment device is shown in Table 2.

Example 9

A hollow fiber membrane type fluid treatment device was formed in the same manner as in Example 1 except for using a tubular housing comprising a first tapered portion having a very small taper angle (0.12°) at the center side of the housing body portion and a second tapered portion having a larger taper angle (6.8°) than that of the first tapered portion at the end portion side, and changing the membrane area at 1.5 m² by using 9,200 hollow fiber membranes. The clearance of the resulting hollow fiber membrane type fluid treatment device is shown in Table 2.

Comparative Example 3

A hollow fiber membrane type fluid treatment device was formed in the same manner as in Example 1 except for using a tubular housing in which the body portion 10A was formed only of a straight portion (but having draft angle) as shown in FIG. 6 and changing the membrane area at 1.5 m² by using 9,200 hollow fiber membranes. The clearance of the resulting hollow fiber membrane type fluid treatment device is shown in Table 2. The results of the dialysate flowability test carried out using the same test specimen are shown in FIG. 7.

In the hollow fiber membrane type fluid treatment devices (hemodialyzers) in the examples and the comparative examples, since the polysulfone hollow fiber membrane having the same performance and feature was used, the difference in data on the examples and the comparative examples shown in the tables was caused only by the difference in the design of the tubular housing.

As shown in Table 2, under the conditions of a blood flow rate of 200 mL/min and a dialysate flow rate of 500 mL/min, the urea clearance and the vitamin B12 clearance of Example 6 were 195.7 ml/min and 146.5 ml/min respectively, the urea clearance and the vitamin B12 clearance of Example 7 were 199.6 ml/min and 165.2 ml/min respectively, the urea clearance and the vitamin B12 clearance of Example 7 were 191.6 ml/min and 135.7 ml/min respectively, and the urea clearance and the vitamin B 12 clearance of Example 9 were 196.8 ml/min and 150.6 ml/min respectively. Specifically, Examples 6 to 9 showed very high values.

On the other hand, the urea clearance and the vitamin B12 clearance of Comparative Example 3 were 174.7 ml/min and 109.0 ml/min respectively, which are lower in comparison with those of the examples.

This is considered to be because the flow of the dialysate in the examples as shown in FIG. 7 is close to an ideal flow (plug flow), that is, the dialysate uniformly flows into the hollow fiber membrane bundle and the substantial membrane area of the hollow fiber membrane bundle with which the dialysate comes in contact is large. Moreover, the standard deviations a of the urea clearance and the vitamin B12 clearance in Examples 6 to 9 are small in comparison with Comparative Example 3. This suggests that the variation in the dialysate flow between the prototype body fluid treatment devices of the examples is small to exhibit excellent properties from the viewpoint product quality control.

Industrial Applicability

In the hollow fiber membrane type fluid treatment device of the present invention, a portion which gradually increases in diameter toward the end face of the housing, that is, a specific baffle plate or end tapered portion, is provided at least on the treatment liquid inlet side of the tubular housing. As a result, the substance removal performance is significantly increased, and the variation in the substance removal performance is little, and occurrence of leakage due to breakage of the hollow fiber membrane is significantly reduced depending on the diameter-expanding portion. Therefore, the hollow fiber membrane type fluid treatment device of the present invention may be suitably used as a hemodialyzer, endotoxin cut filter, or water filtration device in various fields such as a medical treatment field, food field, and industrial field.

TABLE 1

|  |  | Example 1 | Example 2 | Example 3 | Example 4 | Example 5 | Comparative Example 1 | Comparative Example 2 |
|---|---|---|---|---|---|---|---|---|
| Reference figure |  | FIGS. 2, 3 | 61 in FIG. 2 |  |  |  | — | FIG. 5 |
| Number of hollow fiber membranes |  | 9200 | 9200 | 9200 | 9200 | 9200 | 9200 | 9200 |
| Membrane area | m² | 1.5 | 1.5 | 1.5 | 1.5 | 1.5 | 1.5 | 1.5 |
| α | ° | 11.9 | 11.9 | 1.2 | 3.3 | 13.6 | 0 | (0) |
| L1 | mm | 24 | 24 | 24 | 24 | 24 | 24 | 33.7 |
| L2 | mm | 118 | 118 | 118 | 118 | 118 | 118 | 118 |
| L3 | mm | 9.5 | (9.5) | 9.5 | 9.5 | 9.5 | 9.5 | — |
| d1 | mm | 43.0 | 43.0 | 43.0 | 43.0 | 43.0 | 40.5 | 40.5 |
| d2 | mm | 40.1 | (40.1) | 36.5 | 37.2 | 40.7 | 36 | — |
| d3 | mm | 36.1 | 36.1 | 36.1 | 36.1 | 36.1 | 36 | 36 |
| d4 | mm | 32.1 | 32.1 | 32.1 | 32.1 | 36.1 | 33.6 | 33.6 |
| Urea clearance Average | ml/min | 194.5 | 195.1 | 191.6 | 192.8 | 191.1 | 174.7 | 188.2 |
| Variation σ |  | 1.2 | 0.8 | 1.5 | 1.3 | 0.7 | 5.9 | 2.2 |
| Drop leakage occurrence rate |  | 3/10 | 2/10 | 2/10 | 2/10 | 2/10 | 10/10 | 9/10 |

TABLE 2

|  | Example 6 | Example 7 | Example 8 | Example 9 | Comparative Example 3 |
|---|---|---|---|---|---|
| Reference figure | FIG. 4 | FIG. 4 | FIG. 4 | FIG. 4 | FIG. 6 |
| Number of hollow fiber membranes | 9200 | 10100 | 10100 | 9200 | 9200 |

TABLE 2-continued

|  |  | Example 6 | Example 7 | Example 8 | Example 9 | Comparative Example 3 |
|---|---|---|---|---|---|---|
| Membrane area | m² | 1.5 | 1.7 | 1.7 | 1.5 | 1.5 |
| α | ° | 7.6 | 10.8 | 2.2 | 6.8 | 0 |
| L1 | mm | 24 | 24 | 24 | 24 | 24 |
| L2 | mm | 118 | 118 | 118 | 118 | 118 |
| L4 | mm | 15 | 11 | 70 | 15 | 0 |
| L2 − L4 | mm | 103 | 107 | 48 | 103 | 118 |
| (L2 − L4)/(L4) |  | 6.86 | 9.72 | 0.68 | 6.86 | — |
| d1 | mm | 43.0 | 43.4 | 43.4 | 43.0 | 40.5 |
| d3 | mm | 36.1 | 37.8 | 38.9 | 36.1 | 33.6 |
| d4 | mm | 32.1 | 33.6 | 33.6 | 32.5 | 33.6 |
| d4' | mm | — | — | — | 32.1 | — |
| d3/d4 |  | 1.12 | 1.13 | 1.16 | 1.11 | 1 |
| Urea clearance | Average ml/min | 195.7 | 199.6 | 191.6 | 196.8 | 174.7 |
|  | Variation σ | 0.7 | 0 | 1.8 | 0.4 | 8.1 |
| Vitamin B12 clearance | Average ml/min | 146.5 | 165.2 | 135.7 | 150.6 | 109.0 |
|  | Variation σ | 1.3 | 1.3 | 1.6 | 2.3 | 2.2 |

The invention claimed is:

1. A hollow fiber membrane type fluid treatment device for treating blood, the fluid treatment device comprising:
    a housing body portion of a tubular housing containing a single hollow fiber membrane bundle;
    a first housing head portion which is connected with one end of the housing body portion and has a resin layer where the hollow fiber membrane bundle is fixed by using a resin composition, and a first connection port which serves as a treatment liquid inlet;
    a second housing head portion which is connected with a second end of the housing body portion and has a resin layer where the hollow fiber membrane bundle is fixed by using a resin composition, and a second connection port which serves as a treatment liquid outlet;
    first and second header caps attached to the first and second housing head portions, respectively, and the first and second header caps having respective treatment target liquid connection ports; and
    an inner surface of the housing body portion comprises a body straight portion in a center of the housing body portion and an end tapered portion provided at opposing ends of the housing body portion, the end tapered portion increasing in diameter toward an end face of the housing body portion, and hollow fiber membranes of the hollow fiber membrane bundle are arranged so that a distance between individual hollow fiber membranes is gradually increased toward the end face of the housing body portion as the hollow fiber membranes extend along a taper of the end tapered portion, thereby increasing the diameter of the hollow fiber membrane bundle,
    opening ends of the hollow fiber membrane bundle being fixed to an inside of the tubular housing by the resin layers, and the opening ends of the hollow fiber membrane bundle facing the respective treatment target liquid connection ports such that blood flows within the hollow fiber membranes,
    the treatment liquid inlet and treatment liquid outlet being provided at a circumference of the hollow fiber membrane bundle such that a treatment liquid flows outside of the hollow fiber membranes, the hollow fiber membrane bundle configured to allow waste in the blood to be removed through dialysis utilizing one of a diffusion phenomenon resulting from a concentration gradient and filtration resulting from a pressure gradient,
    wherein an angle formed by a centerline of the inner surface of the housing body portion and an inner surface of the end tapered portion is greater than 0° and smaller than an angle defined by $\tan^{-1}\{1/2 \cdot (d1-d4)/L4\}$ (where, d1 is the diameter of the hollow fiber membrane bundle at an end face of the resin layer, d4 is an inner diameter of the body straight portion or minimum diameter portion of the housing body portion, and L4 is the length (one side) of the end tapered portion which increases in diameter toward the end face of the housing body portion), and
    wherein a ratio of the length of the body straight portion to the total length of the end tapered portion is 0.7 to 20, and a ratio of the inner diameter of the end tapered portion at the end face of the housing body portion to the inner diameter of the body straight portion is more than 1 and not more than 3.

2. The hollow fiber membrane type fluid treatment device according to claim 1, wherein the tapered portion comprises a first tapered portion located on the body portion side, and a second tapered portion located on the treatment liquid inlet side, and the angle of the first taper angle is smaller than the angle of the second taper angle.

3. The hollow fiber membrane type fluid treatment device according to claim 1, having a urea clearance and a vitamin B12 clearance of 191 to 200 ml/min and 135 to 170 ml/min, respectively.

4. The hollow fiber membrane type fluid treatment device according to claim 1, comprising baffle plates provided at positions corresponding to the treatment liquid inlet and the treatment liquid outlet of the tubular housing and interspatially from the inner circumference of the tubular housing over the entire inner circumference at a curvature almost along the inner circumference.

5. The hollow fiber membrane type fluid treatment device according to claim 4, wherein the baffle plate gradually increases in diameter toward the end face of the housing.

* * * * *